United States Patent [19]
Seiler et al.

[11] Patent Number: 5,461,212
[45] Date of Patent: Oct. 24, 1995

[54] ASTIGMATIC LASER ABLATION OF SURFACES

[75] Inventors: Theo Seiler, Berlin, Germany; Peter J. Klopotek, Framingham, Mass.

[73] Assignee: Summit Technology, Inc., Waltham, Mass.

[21] Appl. No.: 72,732

[22] Filed: Jun. 4, 1993

[51] Int. Cl.$^6$ ............................. B23K 26/06; B23K 26/02
[52] U.S. Cl. .................. 219/121.68; 219/121.73; 219/121.75; 219/121.85; 606/17; 606/5
[58] Field of Search .................. 219/121.68, 121.72, 219/121.73, 121.75, 121.85; 606/17.5, 11; 128/303.1

[56] References Cited

U.S. PATENT DOCUMENTS

| | | | |
|---|---|---|---|
| 4,387,952 | 6/1983 | Slusher | 350/6.9 |
| 4,732,148 | 3/1988 | Esperance, Jr. | 128/303.1 |
| 4,941,093 | 7/1990 | Marshall et al. | |
| 4,973,330 | 11/1990 | Azema et al. | |
| 5,109,465 | 4/1992 | Klopotek | |
| 5,147,352 | 9/1992 | Azema et al. | |
| 5,256,853 | 10/1993 | McIntrey | 219/121.75 |

FOREIGN PATENT DOCUMENTS

| | | |
|---|---|---|
| 0274205A2 | 7/1988 | European Pat. Off. |
| 0280414A1 | 8/1988 | European Pat. Off. |
| 0296982A1 | 12/1988 | European Pat. Off. |
| 0429368A1 | 5/1991 | European Pat. Off. |
| 0529822A1 | 3/1993 | European Pat. Off. |

*Primary Examiner*—Mark H. Paschall
*Attorney, Agent, or Firm*—Thomas J. Engellenner; Mark A. Kurisko; Lahive & Cockfield

[57] ABSTRACT

Laser surface ablation methods and apparatus are disclosed reprofiling surfaces astigmatically. An optical system includes cylindrically-powered elements to form an elliptical laser irradiation pattern on a target surface. By successively altering the area of the elliptical irradiation, an astigmatic, bi-powered ablation profile is achieved. Preferably, the invention is used with an excimer laser for excimer laser keratoplasty, keratomileusis or other ablative eye surgeries.

17 Claims, 3 Drawing Sheets

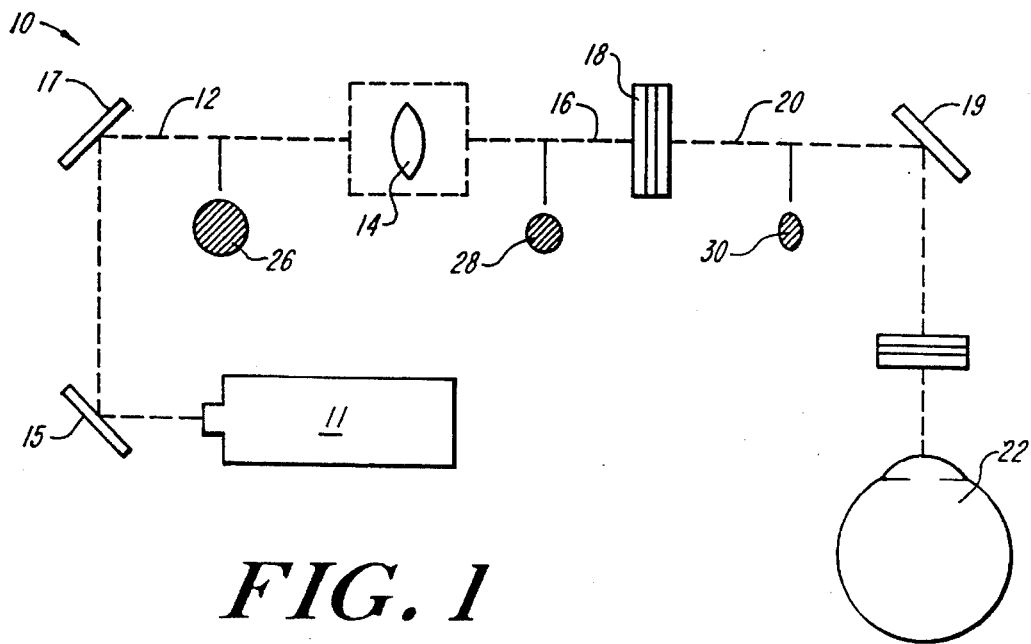
FIG. 1
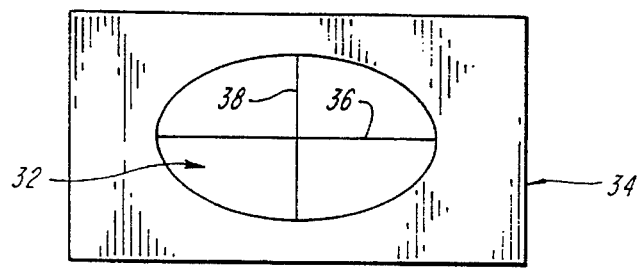
FIG. 2
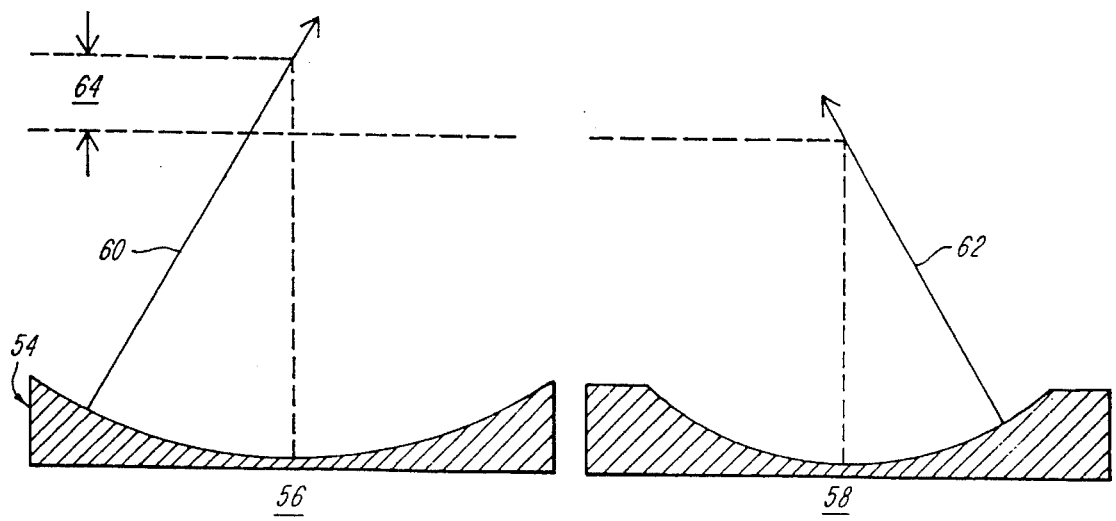
FIG. 4B  FIG. 4A

ASTIGMATIC LASER ABLATION OF SURFACES

BACKGROUND OF THE INVENTION

This invention relates generally to methods and apparatus for eroding or ablating surfaces by lasers. In particular, this invention relates to methods and apparatus for eroding surfaces astigmatically and for the correction of myopic astigmatism through laser keratoplasty or keratomileusis.

Lasers can etch surfaces in a controlled manner. These techniques are known and depend upon the interaction between the surface structure and the laser radiation which has a known wavelength and energy density. In addition, the ablation of a surface by laser radiation is typically time-rate dependent, although this time dependency is usually non-linear with ablative depth because of heat build-up and other artifacts. Therefore, ablative precision is often obtained through the use of pulsed laser radiation. Short pulses provide controlled depth etching in the application area. This control is especially important in keratoplasty or in keratomileusis procedures where the cornea of the eye is ablated to correct certain visual deficiencies, such as near-sightedness. By careful application of laser radiation to the cornea, physicians are able to surgically enhance a patient's vision with precision and without tissue damage by overexposure.

By successive application of laser pulses to a surface and by altering the size of the area under irradiation, curvatures can be created or altered on a surface. For example, when the ablative technique begins by irradiating a large, circular area and progressively decreases the radius of the exposed area, the central region has the greatest ablative depth because it is irradiated the longest. Conversely, the outer-most regions have the least ablative depth. If the surface is initially flat, the resulting profile would be concave. If the surface is initially convex, the surface can be made flat, or the curvature can be reduced depending upon the degree of ablation. In keratoplasty or in keratomileusis, the curvature on the cornea, i.e., the difference between the cornea's ideal curvature and the patient's actual corneal shape, is modified.

Surface erosion techniques to create or remove astigmatic shapes have been less successful. An astigmatic surface is by definition bi-powered: there are two natural and orthogonal curvatures creating the surface. A varying, circular irradiation pattern can only create or remove a single power on a surface. Existing methods to erode astigmatic shapes have been complex and difficult to implement.

For example, U.S. Pat. No. 4,665,913 entitled "Method For Ophthalmological Surgery" discloses methods which provide for different astigmatic shapes through the use of laser scanning. However, this approach is especially difficult to control. The precise control of a reprofiling operation on a surface, e.g., a cornea, using a scanning laser, requires that the laser spot maintain nearly constant spatial intensity and further that the complex etching pattern is carefully followed. However, laser spot intensities are mostly Gaussian and inherently non-uniform. This non-uniformity and the detailed etching pattern leave much room for error, and, thus, require expensive safeguards for surgical applications. Additionally, these methods are naturally time-consuming, since only a small portion of the surface is ablated at a given time.

Another method for eroding an astigmatic surface is provided in U.S. Pat. No. 4,941,093 entitled "Surface Erosion Using Lasers." According to its teachings, specifically configured optical elements or slits are used to provide ablation in one axis, i.e., such that the erosion proceeds selectively relative to a line rather than around a point. Typically, this approach requires a second step to provide spherical correction so that the proper overall curvature is achieved.

Yet another approach involves the use of a graded intensity or photodecomposable mask which varies the laser transmission to the target surface, thereby inducing variable ablative depths on the surface. For example, U.S. Pat. No. 4,856,513 entitled "Laser Reprofiling Systems And Methods" which describes methodology for selectively eroding the cornea through the use of an erodable mask. The mask absorbs the surface laser radiation in varying amounts across the corneal surface to provide the desired surface profiles. This technique though requires the manufacture of a complementary object, i.e., the erodable mask, and also requires precise correlative positioning over the target surface.

It is, accordingly, an object of this invention to provide a simpler method and apparatus for astigmatically reprofiling a surface with an initial, bi-powered, astigmatic shape in order to achieve a new, preferably spherical, shape.

It is another object of this invention to provide a method and apparatus for orienting and adjusting the astigmatic ratio applied to a surface shape with increased control.

It is further an object of this invention to provide a method and apparatus for correcting myopic astigmatism through corneal ablation in laser keratomileusis procedures.

These and other objects of the invention are evident in the description that follows.

SUMMARY OF THE INVENTION

Apparatus and methods are disclosed for astigmatically ablating surfaces in order to impart new profiles and curvatures to such surfaces. A laser means, e.g., a rapidly pulsed laser radiation source, is aligned with a surface to provide photoablative pulses of energy along an optical path to a target region on the surface. A light restricting means, such as an adjustable iris or profiled mask, is disposed within the optical path to spatially control the extent of the laser radiation striking the target surface. Within the optical path, a cylindrical, optical system is also disposed and adjusted to modify the symmetrical laser beam into an elliptical shape for delivery to the target surface.

According to another aspect of the invention, the cylindrically-powered, optical system is rotatable about the laser beam axis. A rotation means is provided for orienting the elliptical shape to a selected axis on the target surface.

According to still another aspect of the invention, the cylindrically-powered, optical system is movable along the axis of the laser beam to modify one axis of the ellipse applied to the target surface to provide for differing astigmatic ratios.

Another aspect of the invention provides the further step of selecting the focal length of the cylindrically-powered, optical system, thereby allowing for the selection of varying astigmatic ratios, as applied to the target surface.

A further aspect of the invention provides a method for correcting corneal astigmatism in keratomileusis procedures. A laser means and, preferably, an excimer laser, is aligned to provide photoablative pulses of energy along an optical path to the patient's cornea. An adjustable iris thin is aligned within the laser beam and optical path behaves as the aperture stop for the laser beam thereby spatially controlling the physical extent of the laser radiation striking the cornea. Within the optical path, a cylindrical optical system is aligned and adjusted to modify the symmetrical laser beam into an elliptical shape for delivery to the cornea.

Various methods and means are disclosed for varying the astigmatic ratio as applied to the corneal surface. In one approach, the cylindrically-powered, optical system is movable along the optical path of the laser beam, thereby altering the astigmatic ratio. Alternatively, different lens or other optical elements (such as cylindrical mirrors) can be substituted for each other to vary the astigmatic ratio as applied to the corneal surface. In this aspect, the focal length of the cylindrically-powered, optical system is selected to alter one dimension of the irradiation ellipse delivered to the cornea.

In yet another aspect, the invention provides a method and means for rotating the cylindrically-powered, optical system to orient the axes of the irradiation ellipse to coincide in an inverse manner with the patient's astigmatic axes.

According to a further aspect of the invention, in a laser system for eroding a surface astigmatically, there is provided a laser means for generating continuous or pulsed laser radiation of photoablative energy. This laser radiation is optically aligned for delivery to a target surface for photoablation. A beam control mechanism adjusts the spatial dimensions of the laser radiation through an iris diaphragm or the like, preferably driven by computer means. The laser energy is further aligned through a cylindrical optical means for adjusting the beam dimensions in one axis of the laser radiation, thereby forming an elliptical shape on the target surface.

In another aspect, the cylindrical optical means can be rotated to rotate the elliptical pattern of laser energy at the target surface for selecting and orienting the astigmatic erosion axis.

In yet another aspect, the cylindrical optical means can be axially shifted to change the size of the elliptical pattern of laser energy at the target surface to select an astigmatic erosion ratio on the surface.

The advantages presented by the features and aspects of the invention are several. In particular, the invention provides an elliptical irradiation pattern to the target surface, enabling simultaneous and bi-powered astigmatic erosion. The inclusion of a cylindrically-powered, optical system within the laser delivery system allows for easy polar orientation and the selection of the astigmatic ablation on a target surface. Applications, such as excimer laser keratomileusis, can take full advantage of the invention by ensuring proper axial orientation of the astigmatic correction applied to the myopic cornea: the accuracy of the orientation is equivalent to the accuracy in which the cylindrically-powered, optical system can be rotated. Furthermore, various astigmatic ratios can be achieved through the selection of the focal length of the cylindrically-powered, optical system; and variable and continuous astigmatic ratios can be achieved through the axial movement of the cylindrical system along the laser beam axis. The normal keratomileusis procedures can then be followed by adjusting the iris diameter to achieve the desired optical correction on the cornea. (The term "adjustable iris" as used herein is intended to encompass various systems for modifying the size of the laser beam, including, for example, adjustable diaphragms, aperture wheels, movable stops and other light restricting mechanisms, as well as optical elements associated therewith to maintain beam homogeneity.)

The invention will next be described in connection with certain preferred embodiments; however, it should be clear that various additions, subtractions and modifications can be made by those skilled in the art without departing from spirit or the scope of the invention. For example, the invention can be used in connection with congenital or other post-operative (e.g., cataract, or penetrating keratoplasty) astigmatisms.

BRIEF DESCRIPTION OF THE DRAWINGS

A more complete understanding of the invention may be obtained by reference to the drawings in which:

FIG. 1 is a diagrammatic illustration of apparatus for practicing a method of eroding a target surface astigmatically, in accordance with the invention:

FIG. 2 illustrates the elliptical laser beam irradiation used to erode a surface astigmatically;

FIGS. 4A and 4B illustrate curvatures created in orthogonal axes through surface erosion by elliptical laser irradiation;

DETAILED DESCRIPTION

Figure 3A:
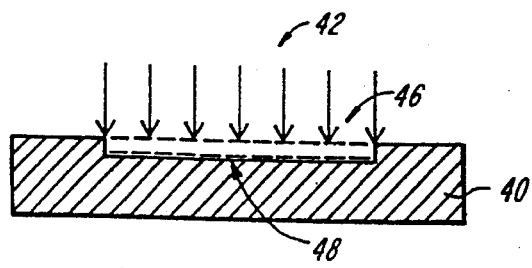
FIGS. 3A through 3F illustrate diagrammatically the successive steps needed to etch a target surface astigmatically with elliptical irradiation.

FIG. 1 illustrates a system 10 according to the invention for delivering an elliptical beam of ablative laser energy to a target surface. In FIG. 1, a laser means 11 provides radiation output 12 to a beam control optical system 14 which modifies the shape and size of the laser beam 16. This beam is aligned to a cylindrically-powered, optical system 18 to uniaxially modify the size and shape of the laser beam 20 for delivery to the target surface 22. FIG. 1 also shows cross-sectional views 26, 28, and 30 of the laser beam as it is transformed into its various shapes 12, 16, 20. The beam 12, leaving the laser means 11, will typically have a circular beam shape 26. The beam 16, leaving the beam control optical system 14, will typically have a circular beam shape 28. The beam 20 leaving the cylindrically-powered, optical system 18 will form an elliptical pattern on the target surface 22, as shown in its cross-sectional view 30.

The optical systems 14 and 18 are coaxially aligned to the laser means 11 so as to provide optimum and unaberrated throughput to the target surface 22. Mirrors 15, 17 and 19 permit the system to operate in a folded configuration. The laser means 11 can provide continuous or pulsed laser radiation output 12 to the beam control optical system 14. An afocal beam expander with a controllable aperture stop can comprise the beam control optical system 14 to change the cross-sectional diameter of the laser beam 12 into a larger or smaller size (e.g., the illustrated view 28 shows a smaller size) and to provide highly collimated output for the cylindrically-powered, optical system 18. This cylindrical system 18 provides optical power in one axis only, and modifies the laser beam 16 from a circular profile 28 to an elliptical one 30. Both systems 14 and 18 can have controllable aperture stops to adjust the beam dimensions delivered to the target surface 22. By adjustment of the two aperture stops, the major and minor axis dimension of the elliptical beam 30 can be adjusted, thereby fitting the astigmatic dimensions of the target surface 22.

The construction of the system shown in FIG. 1 can be made in several ways. Both optical systems 14 and 18 can be made of simple elements. For example, the beam control optical system can comprise a simple lens with an adjustable iris disposed to control the symmetrical beam shape 28. Alternatively, the beam control system 14 can also include a beam clipping mechanism, a light homogenizer and/or a beam expander, or these functions, if desired, can be performed by separate optical elements prior to beam shaping in optical system 14. The cylindrical system 18 can, likewise, be made of a simple lens, like a cylindrical lens or mirror, or can, likewise, include additional beam conditioning elements. This system 18 can be used to adjust one dimension of the elliptical laser profile 30 at the target surface 22.

Since the cylindrically-powered system 18 provides optical power in one axis only, one method of adjusting the elliptical dimension is to axially shift the system 18. The system 18 will cause the beam 16 to diverge, if the system 18 is negatively powered. Thus, shifting the system 18 axially will cause one dimension of the ellipse 30 to change on the target surface 22, since the beam 20 will diverge or converge over some distance to reach the surface 22. With accurate control of the axial movement, accurate sizing of the elliptical shape 30 can be achieved. The elliptical shape provides the means to etch a surface astigmatically.

The orientation of the ellipse 30 is also controllable, according to the methodology presented in accordance with the invention. As depicted in FIG. 1, the major axis of the ellipse 30 is vertical. In the illustration, such a pattern can be created either through a negatively-powered, cylindrical system 18 in the vertical axis or through a positively-powered, cylindrical system 18 in the orthogonal axis. In either case, when the system 18 is rotated about the optical axis of the laser beam 16 and 20, the orientation of the ellipse also changes. According to this technique, the ellipse can be oriented to fit the desired astigmatic axis on the target surface 22.

It should be appreciated that systems 14 and 18 can be combined in some implementations. The combined optical system would simply require that at least one optical element has astigmatic power. The combined system could be axially shifted in the same manner and disposed with a single aperture stop to create the ellipse 30 in a controller manner. Alternatively, the combined system can be stationary and used in conjunction with a series of apertures, e.g., on a wheel or the like. Furthermore, rotating the combined system will also adjust the orientation of the ellipse on the target surface 22.

In a preferred embodiment, the overall system of FIG. 1 can be used in excimer laser keratomileusis. According to this preferred embodiment, the laser means is a rapidly pulsed UV laser source, and the target surface is the human cornea, optically aligned to the laser means. The laser means, for example, can be an excimer laser, and one preferred embodiment is an Argon-Fluoride laser having a characteristic emission wavelength of about 193 nanometers. Other pulsed UV lasers having both shorter wavelengths down to about 157 nm (e.g., a Fluoride laser) and longer wavelengths up to about 300 nm.

For example, in the case of eroding either Bowman's membrane or the stromal portion of the cornea by energy of wavelength 193 nm (the wavelength obtained from an ArF Excimer laser), the threshold value is about 50 mJ per cm$^2$ per pulse, and the saturation value is about 250 mJ per cm$^2$ per pulse. Suitable energy densities at the corneal surface are 50 mJ per cm$^2$ to one J per cm$^2$ per pulse for a wavelength of 193 nm.

The threshold value will vary with wavelength, and at 157 nm, which is the wavelength obtained from an F$_2$ laser, the threshold is about 5 mJ per cm$^2$ per pulse. At this wavelength, suitable energy densities at the corneal surface are 5 mJ per cm$^2$ to one J per cm$^2$ per pulse.

Most preferably, the laser system is used to provide an energy density at the surface to be eroded of slightly less than the saturation value. Thus, when eroding the cornea with a wavelength of 193 nm (under which conditions the saturation value is 250 mJ per cm$^2$ per pulse), it is preferable to provide to the cornea pulses of an energy density of 100 to 150 mJ per cm$^2$ per pulse. Typically, a single pulse will erode a depth in the range 0.1 to 1 micrometer of tissue from the cornea.

The pulse repetition rate for the laser may be chosen to meet the needs of each particular application. Normally the rate will be between 1 and 500 pulses per second, preferably between 1 and 100 pulses per second. When it is desired to vary the beam size, the laser pulses may be stopped. Alternatively, the beam size may be varied while the pulses continue. If a measurement device is used to monitor the erosion progress and control the laser system automatically, the beam size may be varied continuously at a controlled rate without interrupting the pulses.

Suitable irradiation intensities vary depending on the wavelength of the laser, and the nature of the irradiated object. For any given wavelength of laser energy applied to any given material, there will typically be a threshold value of energy density below which significant erosion does not occur. Above the threshold density, there will be a range of energy densities over which increasing energy densities give increasing depths of erosion, until a saturation value is reached. For increases in energy density above the saturation value, no significant increase in erosion occurs.

The threshold value and the saturation value vary from wavelength to wavelength of laser energy and from material to material of the surface to be eroded, in a manner which is not easily predictable. However, for any particular laser and any particular material, the values can be found readily by experiment.

With reference again to FIG. 1, the patient's astigmatic axis can be fit to the elliptical beam profile 30 through the rotation of the cylindrical system 18. An aperture stop disposed within the optical system 14 can control the one dimension of the ellipse 30 at the corneal target surface 22. Positioning the cylindrical system 18 axially can further control the other dimension of the ellipse 30. It is also preferable that the system 10 produce an output beam 20 having a substantially constant energy per unit area regardless of its varying size. For further details on basic laser keratomileusis systems and methods, as well as techniques for ensuring substantial constant energy density, see U.S. Pat. Nos. 4,941,093 and 4,856,516, both of which are incorporated herein by reference.

The control of the dimension of the ellipse along the axis with the cylindrical power can also be achieved through the selection and/or replacement of particular optical elements with system 18. According to this embodiment, by selecting cylindrical elements with different optical powers (i.e., different focal lengths) for placement within the system shown in FIG. 1, variable elliptical dimensions can be achieved. This methodology is equivalent to adjusting the axial placement of the system 18.

FIG. 2 illustrates the elliptical shape 32 of the laser energy striking the target surface 34. The difference between major axis 36 and the minor axis 38 of the ellipse 32 provides the means to erode a surface astigmatically. To create the desired surface etch, the surface 34 is irradiated with a laser which has ablative properties while the dimensions of the ellipse are altered. The ratio between the major and minor axes is held constant while the overall area of the ellipse 32 is changed.

Figure 3D:
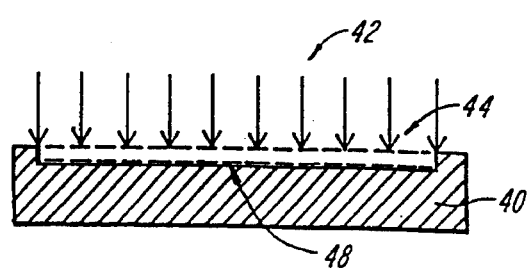
Figure 3B:
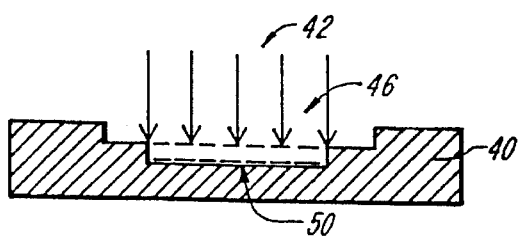
Figure 3E:
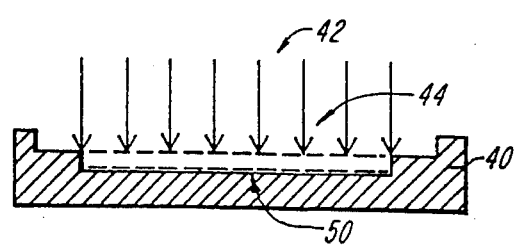
Figure 3C:
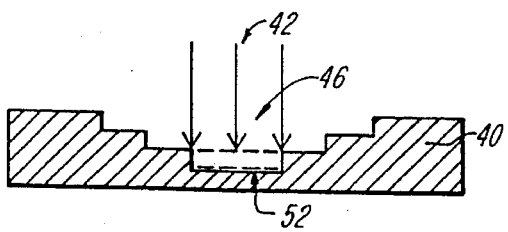
Figure 3F:
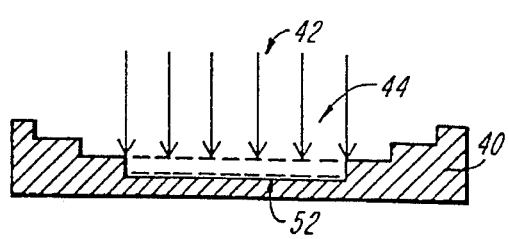

FIGS. 3A–3F illustrate how the elliptical pattern can erode a surface astigmatically. The target surface 40 is irradiated by the elliptical laser beam 42. The major axis 44 of the beam irradiates a wider dimension on the target surface 40 than does the minor axis 46. After a predetermined period of time, the laser beam etches away the part 48 of the target surface 40 which was under irradiation. Then the area of the ellipse is modified by reducing the size of the major axis 44 and minor axis 46, but at the same time keeping the ratio between the two constant. Typically, the laser beam 42 is inactivated or blocked by a shutter while the exposed area is adjusted. After another period of time, another part 50 of the target surface is removed through laser etching. The area of the ellipse is adjusted again, as described in FIG. 1, to etch another part 52 from the target surface 40. FIGS. 3A–3C illustrate the cumulative effect along one axis of the elliptical beam while FIGS. 3D–3F illustrate the cumulative effect along the other axis.

FIGS. 4A and. 4B illustrate the end result of the process described in FIGS. 3A–3F, with successive elliptical irradiations on a planar target surface 54. The target surface has a larger diameter 56 etched pattern along the axis irradiated by the major axis of the ellipse and a smaller diameter 58 etched pattern on the minor axis of the ellipse. By reducing the area of the ellipse in a controlled manner and while keeping the ratio between the major and minor axis fixed, two distinct optical powers can be created on the target surface 54. As shown in FIG. 4A, the major axis has a larger radius of curvature 60, and as shown in FIG. 4B, the minor axis has a smaller radius of curvature 62. The difference between the two radii 64 is approximately a linear function of the amount of astigmatic power created on the surface 54 through the laser erosion.

Figure 5A:
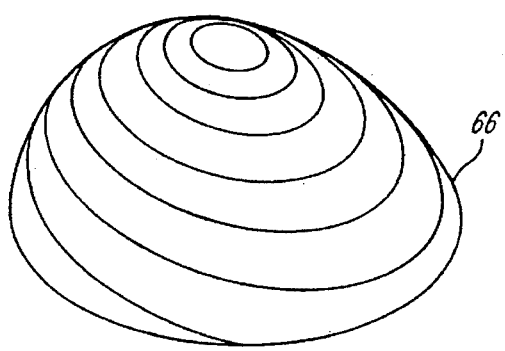
FIGS. 5A and 5B are perspective views of an astigmatic myopic corneal surface, before and after reprofiling, respectively.
Figure 5B:
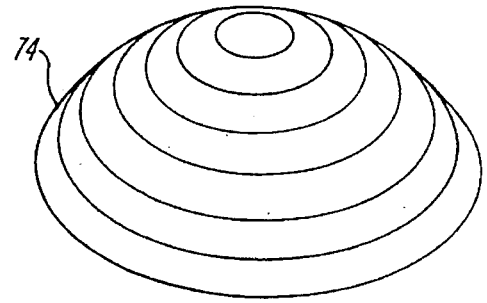

FIGS. 5A and 5B illustrate how the cornea of an astigmatic, myopic eye can be reprofiled to achieve a desired optical power and spherical refraction. Consider the astigmatic cornea 66 shown in FIG. 5A as composed of a series of layers. Each layer can be removed with one or more laser pulses, depending upon the laser and material. After a layer is removed, the irradiation area is altered to remove a different sized layer in a successive irradiation. Controlling the size of the laser irradiation on the cornea through sequential layer etches creates the desired profile 74, shown in FIG. 5B. The contour lines, shown in both FIG. 5A and 5B, represent lines of equal topographic height on the corneal surface before and after treatment, respectively.

The varying aperture profile of successive laser irradiations is geometric. For one axis, $$t = R - \sqrt{R^2 - \frac{D^2}{4}}$$

where t is the height of the eye surface (measured from a base plane which intersects the eye at a diameter D), D is the outer diameter of the ablated surface area and R is the resultant, one-dimensional radius of the surface 66. The only portion of the surface 66 which is of interest is the dimension D, which is initially under the laser irradiation. Once t is determined, the successive sizes of the ellipse to remove each layer can be determined. For example, one laser pulse can etch away Δt in thickness from the target surface 66..By replacing t with t–Δt, a smaller linear dimension D is determined.

The rate of change in the size of the elliptical exposure area depends upon the selected radius of curvature 74 for the surface erosion. For one dimension, the power of a surface can be described in terms of Diopters (1/meter units), the typical terminology for vision correction. A Diopter is defined as $$\text{Diopter} = \frac{n' - n}{R}$$

where n and n' are the wavelength dependent optical indexes of refraction before and within target surface 66, respectively. R is the radius of the surface. In excimer laser keratoplasty or keratomileusis procedures, the index n of the incident medium is air, with an index of approximately 1. The index of the average human cornea, i.e., n', is approximately 1.376 for visible light. If a patient needs a −3.0 Diopter correction, the radius of the surface erosion is about 125.33 mm. The successive irradiations on the cornea are, therefore, adjusted in size to erode the surface 66 to that radius.

If a patient has myopic astigmatism, or more commonly called astigmatic near-sightedness, both axes of the cornea can be eroded simultaneously to perform a bi-powered erosion. If, for example, a −3.0 Diopter correction is needed in one axis and a −3.9 Diopter correction is needed in the orthogonal axis on the cornea, the corresponding irradiation size of the elliptical excimer laser beam is about 4.6 mm and about 4.1 mm, respectively. The thickness t of the cornea removed during the ablation will vary depending upon size of the optical zone being reprofiled. The procedure can be largely confined to erosion of the Bowman's layer of the cornea, if desired, by choosing a small optical zone for reprofiling. Alternatively, a larger optical zone may be desired and, in such case, penetration into the stromal region of the cornea will typically occur. Generally, it is desirable to avoid ablation of more than 100–200 microns of the cornea, in any event.

Figure 6:
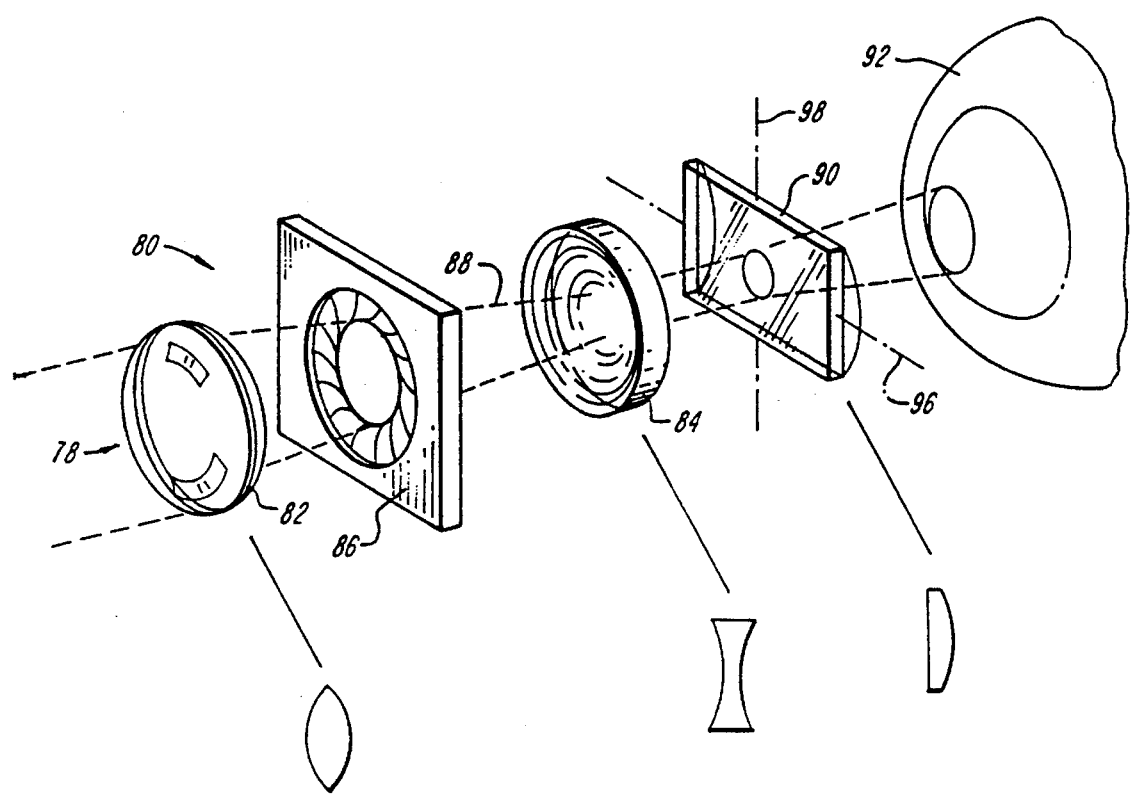
FIG. 6 is a more detailed schematic view of a laser ablation system in accordance with the invention.

FIG. 6 is a more detailed illustration of one embodiment of the invention. A laser beam 78 enters a beam control optical system 80, which is optically aligned to the beam 78. The beam control optical system 80 is an afocal system, producing collimated radiation of a different radius than the input while maintaining substantially constant energy density regardless of the beam dimensions. A positive lens 82 and negative lens 84 positioned at a distance equal to the sum of their respective focal lengths can create such a system. An aperture 86 limits the diametrical extent 88 of the laser beam 78 transmitted through the beam control optical system 80. The laser beam 78 entering the cylindrically-powered, optical system 90 is collimated and circular where it is modified in one axis for delivery to the target surface 92. The aperture stop 86 can change the diameter of the laser beam 78 in several ways. For example, through a computer driven mechanism, the diameter of the aperture can be altered, e.g., by an adjustable iris diaphragm or the like. Or equivalently, the axial movement of the aperture 86 can alter the beam 78 diameter exiting the beam control optical system 80.

FIG. 6 also shows a construction of the cylindrically-powered, optical system 90. One axis 96 does not alter the size or shape of the laser beam 78. The other axis 98 contains a cylindrical correction power element. Varying astigmatic ratios can be achieved by adjusting the position of element 90 axially.

The polar orientation of the ellipse on the eye can be adjusted through rotation of the cylindrically-powered, optical system 90 about the laser beam 78 axis to fit the astigmatic axes of the surface or, for example, to fit the astigmatic axes of the myopic patient in keratoplasty or keratomileusis surgery.

Figure 7:
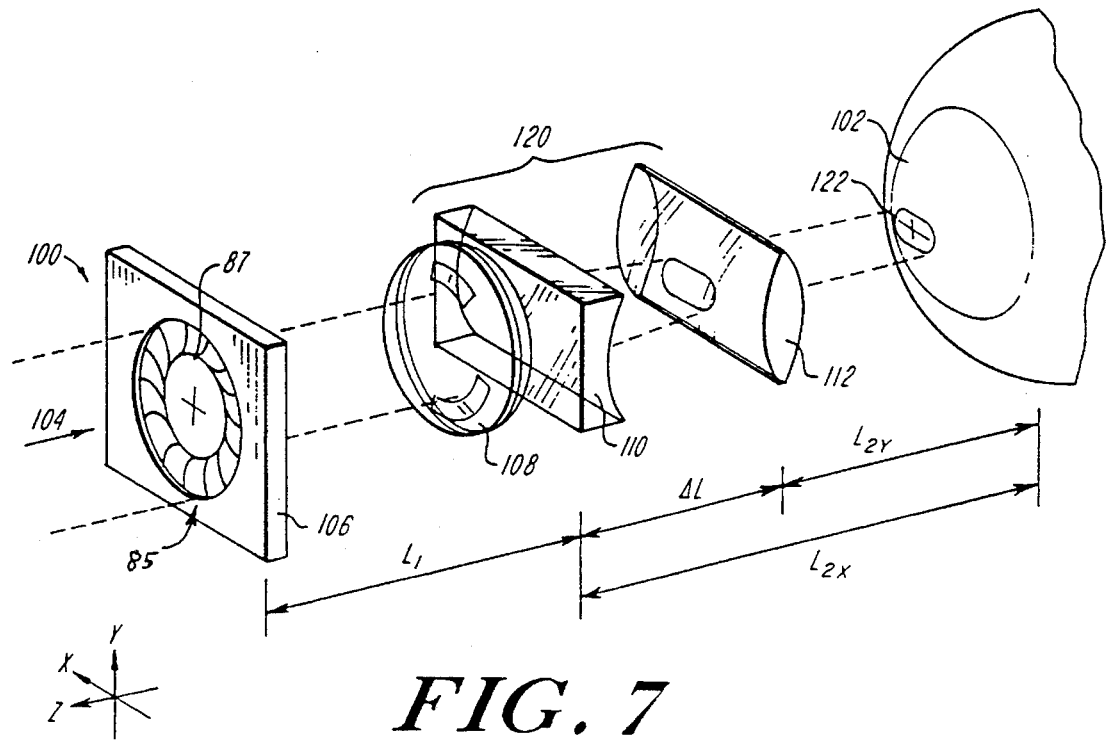

FIG. 7 is another embodiment of the invention in which the system 100 not only delivers an elliptical beam of ablative laser radiation to a target surface 102 but also ensures that the image plane is unchanged for both optical axes (as defined by the orientation of cylindrical lenses 110 and 112). A laser beam 104 enters a beam control optical system 80 (which is simply illustrated as an adjustable iris 85 having an aperture 87, although it may include additional elements, such as matched positive and negative lenses as illustrated in FIG. 6, or a combination of lenses and an adjustable stop), again producing a collimated radiation output of a different radius than the input while maintaining substantially constant energy density regardless of the beam dimensions.

In FIG. 7, a cylindrically-power optical system 120 is employed to image the aperture of the beam control system 80 in a plane substantially parallel to the aperture plane (e.g., perpendicular to the beam axis). As illustrated the cylindrically powered optical system 120 includes a spherical lens 108, a cylindrical lens with negative focal power 110 and a complementary cylindrical lens with positive focal power 112. (Lenses 108 and 110 can, of course, be designed as a single lens with one surface spherical and the other cylindrical. This simplification would reduce the number of components and result in smaller losses of beam energy. However, for purposes of illustration and explanation of underlying principles, the lenses 108 and 110 are shown as two separate elements.)

For purposes of simplified explanation, assume that lenses 108 and 110 are either formed as a single unit or separated by negligible distance. The magnification, $M_x$, on the X axis, which is not affected by cylindrical lenses 110 and 112, is defined by the following formula $$M_x = \frac{L_{2x}}{L_1}$$

In one preferred embodiment, spherical lens 108 and cylindrical lens 110 are chosen, such that their combined focal power on the Y axis is equal to $L_1$. If lenses 108 and 110 are close to each other, the focal length of cylindrical lens 110 (which will be negative) can be defined by the following equation.

$$f_{110} = \frac{1}{1/L_1 - 1/f_{108}}$$

This results in "parallel beam processing" along the Y axis in the region between the first (negative) cylindrical lens 110 and the second (positive) cylindrical lens 112. The distance $\Delta L$ between lens 110 and lens 112 is then chosen, such that the length of the final span $L_{2y}$ between lens 112 and the target is chosen.

The distance $\Delta L$ between lenses 110 and 112 is chosen, such the remaining distance $L_{2y}$ between lens 112 and the target is defined as follows:

$$f_{112} = L_{2y}$$

and the magnification along the Y axis $M_x$ is:

$$M_x = \frac{L_{2y}}{L_1}$$

which will always be less than $M_x$.

It should be clear that the use of spherical lens 108, and the two cylindrical lenses 110 and 112, permits the clinician to rotate the axis of cylindrically around Z axis while maintaining the image of aperture in a plane substantially parallel to the plane of aperture 87. In general, the use of two cylindrical lenses of opposite power will allow this afocal magnification effect so long as both cylindrical lenses are sufficiently separated from each other.

The image spot 122 shows schematically that the dimension of the image in the Y axis is smaller than the dimension in the X axis. By rotating the entire assembly 120, the asymmetry can be fitted to any particular astigmatic axis, to selectively ablate the cornea and correct for a particular astigmatic problem.

It should also be clear that changes in the image magnification $M_y$ can be accomplished by either axial movement of one or more lens elements, or by swapping one cylindrical lens, (e.g., lens 112), with another having a different focal power and positioning the lens to satisfy the conditions outlined above. In essence, the free space between lenses 110 and 112 is a buffer in which to accommodate variations in the Y axis magnification.

Since swapping lens element 112 for another discrete lens element may be difficult or time consuming in practice, continuous variation of My also can be accomplished by replacing the simple lens 112 with a variable cylindrical zoom lens.

What is claimed is:

1. A method for ablating a surface astigmatically by laser energy, the method comprising the steps of:

aligning a surface with a laser means, which is operable to deliver a beam of photoablative pulses of laser energy along a path to the surface;

varying the size of the beam;

disposing a cylindrically-powered, optical system along said beam path such that a beam of laser energy passing through the cylindrical system is shaped into an elliptical form having a major and a minor axis;

adjusting the axial position of said cylindrically-powered, optical system along said beam path to select an astigmatic ratio of said major and minor axes on said surface; and operating said laser while varying the beam size to deliver a radiation beam to said cylindrically-powered, optical system thereby forming a time-varying, elliptical distribution of energy on said surface.

2. The method of claim 1 wherein the method further comprises rotating a cylindrically-powered, optical system to select the orientation of said elliptical distribution of energy on said surface for the astigmatic erosion.

3. A method according to claim 1 wherein the method further comprises varying the size of the beam with an adjustable aperture and imaging the aperture onto said surface.

4. A method according to claim 1 wherein the method further includes the step of adjusting the focal length of said cylindrically-powered, optical system to select the astigmatic ratio on said surface for the astigmatic erosion.

5. A method for providing astigmatic ablation to an area of the cornea of an eye for correcting myopic astigmatism, the method comprising the steps of:

fixing an eye relative to laser means operable to deliver a beam of photoablative pulses of laser energy along a path to said cornea;

varying the size of the beam;

disposing a cylindrically-powered, optical system along said beam path such that a beam of laser energy passing through the cylindrical system is shaped into an elliptical form having a major and a minor axis;

adjusting the axial position of said cylindrically-powered, optical system along said beam path to select an astigmatic ratio of said major and minor axes on said cornea; and operating said laser while varying the beam size to deliver a radiation beam to said cylindrically-powered, optical system thereby forming a time-varying, elliptical distribution of energy on said cornea.

6. A method according to claim 5 wherein the method further comprises rotating a cylindrically-powered, optical system to orient said elliptical distribution of energy on said cornea.

7. A method according to claim 5 wherein the method further comprises varying the size of the beam with an adjustable aperture and imaging the aperture onto said cornea.

8. A method according to claim 5 wherein the method further includes the step of adjusting the focal length of said cylindrically-powered, optical system to select the photoablative astigmatic ratio on said cornea.

9. A method according to claim 5 in which said laser means employs an excimer laser.

10. A method according to claim 5 in which said cylindrically-powered, optical system is a cylindrical lens.

11. A laser system for astigmatically reprofiling a surface, said laser system comprising:

laser means for generating pulses of laser light along a beam path at an energy level, such that the pulses can be absorbed at a surface to induce photoablation;

beam control means for controlling said beam dimensions at said surface;

cylindrically-powered optical means disposed along the beam path for adjusting said beam dimensions in one axis for creating an astigmatic irradiation pattern at said surface; and adjustment means for axially shifting said cylindrically-powered, optical means to select an astigmatic ratio to be applied to said surface.

12. A laser system according to claim 11 wherein said beam control means includes an adjustable iris for controlling the diameter of said laser beam.

13. A laser system according to claim 11 wherein said cylindrically-powered, optical means further comprises means for rotating at least one cylindrically-powered, optical elements to orient an astigmatic axis on said surface.

14. A laser system according to claim 12 wherein said cylindrically-powered, optical means further comprises a first cylindrical lens having a negative focal power and a second cylindrical lens having a positive focal power for imaging the adjustable iris onto said surface.

15. A laser system according to claim 11 wherein said beam control means is afocal and further includes a beam stop which is movable along said laser beam axis for controlling the diameter of said laser beam applied to said surface.

16. A laser system according to claim 11 wherein the laser means is an excimer laser.

17. A laser system according to claim 16 wherein the excimer laser is an Argon Fluoride laser.

* * * * *